United States Patent [19]

Yachia et al.

[11] Patent Number: 4,523,584
[45] Date of Patent: Jun. 18, 1985

[54] PENILE ERECTILE SYSTEM

[75] Inventors: Daniel Yachia, Ramat Efal, Israel; Henry W. Lynch, Racine, Wis.

[73] Assignee: Medical Engineering Corporation, Racine, Wis.

[21] Appl. No.: 472,155

[22] Filed: Mar. 4, 1983

[51] Int. Cl.³ .............................................. A61F 5/00
[52] U.S. Cl. ...................................................... 128/79
[58] Field of Search ......................................... 128/79

[56] References Cited

U.S. PATENT DOCUMENTS

| 4,201,202 | 5/1980 | Finney et al. | 128/79 |
| 4,204,530 | 5/1980 | Finney | 128/79 |
| 4,281,648 | 8/1981 | Rogers | 128/79 |
| 4,369,771 | 1/1983 | Trick | 128/79 |
| 4,407,275 | 10/1983 | Schroeder | 128/79 |

FOREIGN PATENT DOCUMENTS 835637 4/1952 Fed. Rep. of Germany.

Primary Examiner—Dalton L. Truluck
Attorney, Agent, or Firm—Quarles & Brady

[57] ABSTRACT

A penile erectile system for treating male impotency comprises a sleeve of biocompatible material having at least one pressurizable chamber which is adapted to be implanted about the penile shaft of a patient beneath the penile skin between the skin and the shaft, a fluid reservoir of pressurizing fluid, and a pump for transferring the fluid under pressure from the reservoir to the chamber. The system also includes tubing connecting the reservoir and pump to the pressurizable chamber and a valve for controlling the flow of fluid into and out of the pressurizable chamber. In a preferred embodiment, a pressure bulb serves both as the fluid reservoir and the pump.

11 Claims, 7 Drawing Figures

PENILE ERECTILE SYSTEM

The present invention relates to a penile erectile system. More particularly, it relates to an inflatable, implantable penile erectile system.

DESCRIPTION OF THE PRIOR ART

There are some cases of erectile impotence for which the surgical implantation of a penile erectile system is the only practical means of remedying the impotency. In such cases in the past, several different types of implantable penile erectile systems have been employed.

One type of implantable penile erectile system which has been used is an inflatable system which includes two inflatable and distensible tubes each of which is surgically implanted in a separate corpus cavernosum of the penis. Each of the tubes is connected by tubing to a relatively large reservoir of inflating and pressurizing fluid which is implanted elsewhere in the body. An erection is achieved by inflating and pressurizing the distensible tubes. The devices of Buuck U.S. Pat. No. 3,954,102 and Uson U.S. Pat. No. 4,009,711 are representative of inflatable penile erectile systems.

Another type of penile erectile system comprises a pair of rods of suitable stiffness which are surgically implanted into the corpora cavernosa of the penis. A significant advantage of this system is that the amount of surgery involved is minimal as there is no fluid reservoir to implant. A disadvantage of this system is that the permanent stiffness of the rods can be a source of physical pain and embarrassment to the patient. Representative penile erectile systems employing rod implants are disclosed in Small et al. U.S. Pat. No. 3,893,456 and Finney et al. U.S. Pat. No. 4,066,037.

Another implantable erectile system which combines some of the features of both the inflatable system and the rod-type system is disclosed in Finney U.S. Pat. No. 4,201,202. The system disclosed therein includes a rod within a sleeve positioned about the rod to form a chamber. An erection is achieved by pressurizing the chamber with fluid to make it stiff and thus to straighten and support the rod. The chamber is depressurized by use of a pressure control valve.

A common disadvantage of all of the foregoing systems is that in each of them either tubes or rods are implanted into the corpora cavernosa replacing the spongy tissue and thus making the operation irreversible.

SUMMARY OF THE INVENTION

It is the general object of the present invention to disclose a novel implantable penile erectile system.

It is a further object to disclose a novel implantable penile erectile system which can be implanted without replacing the spongy tissue essential for a normal erection.

The penile erectile system of the present invention consists of a pressurizable sleeve which can be surgically implanted around the penile shaft under the penile skin, between the penile shaft and the skin, a reservoir for pressurizing fluid, a pump, and valve means for controlling the flow of fluid to the sleeve.

The sleeve is preferably comprised of two layers of a biocompatible material, such as silicone rubber, which are sealed together along their borders to form at least one pressurizable chamber. To achieve even inflation and rigidity, the layers are preferably further sealed within their borders to form a plurality of divided, interconnected longitudinal chambers.

In one embodiment, the layer of material forming the outer layer is elastic and distensible and the layer forming the inner surface, when the sleeve is placed about the penile shaft, is of a higher modulus, stiffer and less elastic material. When this embodiment is pressurized the outer layer stretches or distends outwardly so that the sleeve causes an expansion in the girth of the penis, as well as a stiffening of the shaft.

The sleeve can be supplied in various shapes and sizes. The sleeve selected for use in a patient should be long enough to extend from the arcuate pubic ligament of the patient to the corona of the glans and of a width sufficient to cover the corpora cavernosa. In order to minimize buckling on the underside when the penis is flaccid, the width of the sleeve should be such that the pressurizable portion of the sleeve does not cover the urethra. To keep the sleeve in place, the two longitudinal sides of the sleeve may be joined together by mesh, webbing or single layer of membrane. When a single layer membrane is used to join the two longitudinal sides of the sleeve, it is preferred to use a very low modulus (stretchy) high elongation material. When the low modulus membrane is attached to the sides of the sleeve the membrane should be stretched longitudinally about 50% so that in repose it will pull the sleeve into a normal pendant position, without wrinkling or folding. Alternatively, the longitudinal sides of the sleeve may be provided with suture tabs or other anchoring means.

The penile erectile system of the present invention also includes a reservoir for pressurizing fluid, a pump, and valve means which opens to permit pressurizing fluid into the chamber of the sleeve and then closes to retain the fluid in the chamber. When it is desired to depressurize the chamber the valve is opened to permit the pressurizing fluid to return to the reservoir. The various components of the system are connected together with tubing to form a closed system.

The foregoing and other objects and advantages will become apparent from the drawings and description which follow:

DESCRIPTION OF THE PREFERRED EMBODIMENTS

Figure 1:
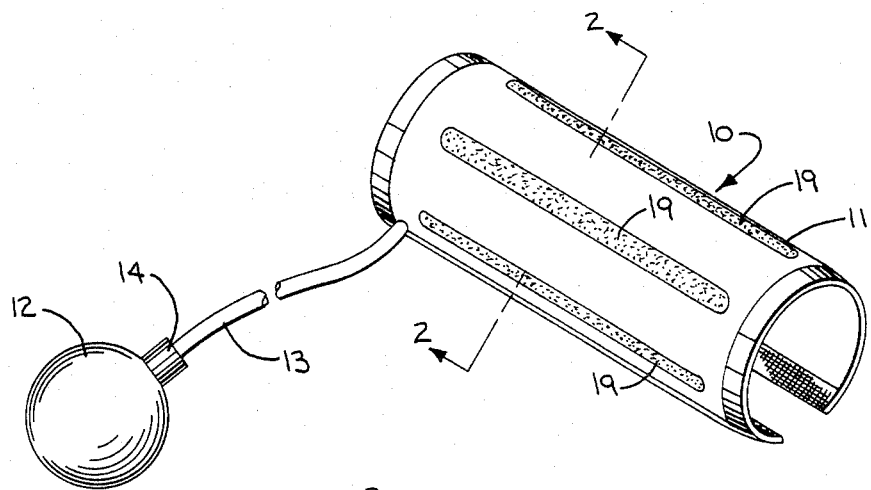
FIG. 1 is a perspective view of the preferred embodiment of the penile erectile system of the present invention.

Referring now to FIG. 1, the preferred embodiment of the penile erectile system 10 is seen to comprise a sleeve 11, a pressure bulb 12 which serves as a combined fluid reservoir and pump, a length of tubing 13 connecting the pressure bulb 12 to the sleeve implant 11 and a valve 14 located along the tubing between the pressure bulb 12 and sleeve 11.

Figure 2:
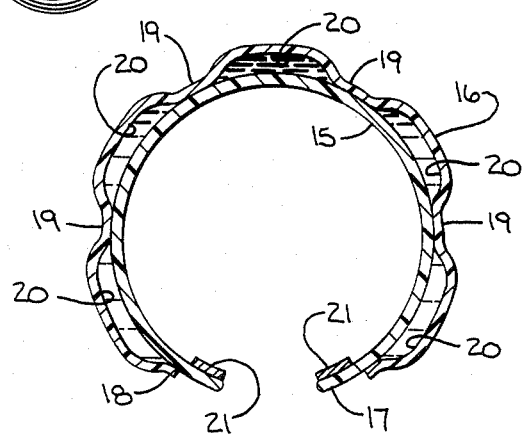
FIG. 2 is a sectional view taken along lines 2—2 of FIG. 1.
Figure 3:
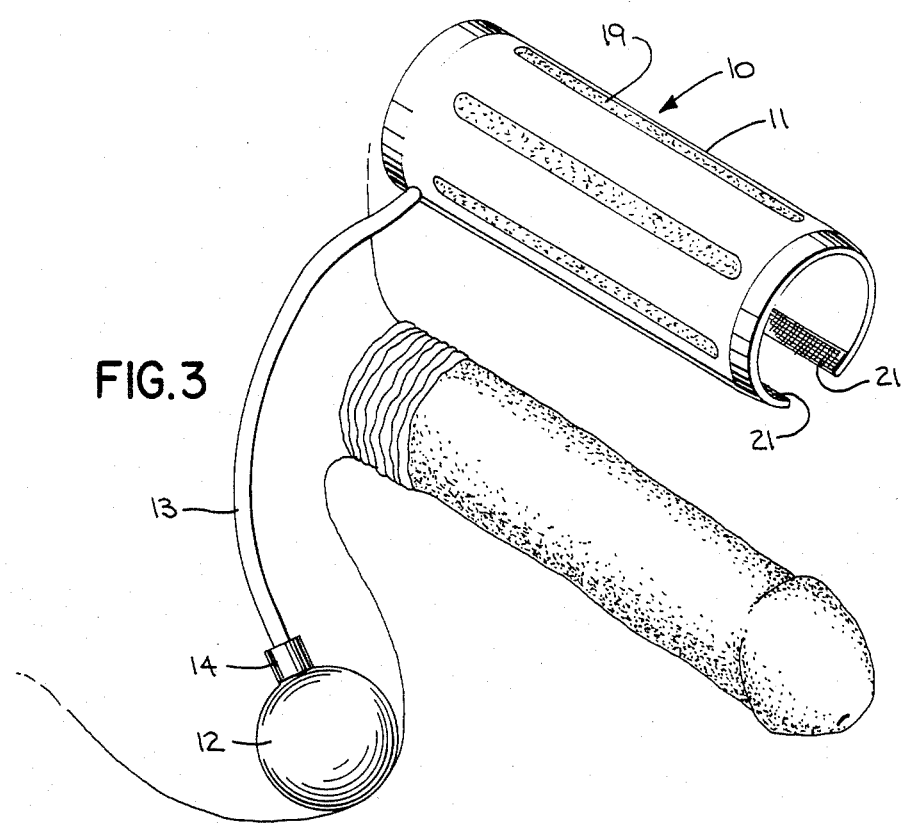
FIGS. 3 and 4 are perspective views showing the embodiment of FIG. 1 and the method of implantation.

As seen best in FIG. 2, the main body of the sleeve 11 is comprised of an inner wall 15 and an outer wall 16 which are sealed together at their borders 17, 18, and at points 19 within their borders to form a plurality of longitudinally divided chambers 20 seen in FIGS. 1 and 3. The chambers 20 are interconnected so that they are all pressurized when the bulb 12 is squeezed.

Still referring to FIGS. 1 and 3, it can be seen that suturing strips 21 are attached to the inner wall 15 of the sleeve implant 21 adjacent the edges 17 and 18. The suturing strips 21 are used to anchor the sleeve 11 in place.

In the preferred embodiment, the inner wall 15 of the sleeve 11 is of a relatively inelastic material and the outer wall 16 is more elastic. Thus, when the chambers 20 in the sleeve 11 are pressurized the outer wall 16 will stretch or distend to increase the penile girth. The inelastic inner wall 15, however, will not stretch and exert excessive pressure on the penis. The inner wall 15 may be made relatively inelastic by making it thicker than the outer wall 16 or using as the material of the inner wall 15 a silicone coated mesh or woven fabric of limited distensibility. The outer wall 16 may be of relatively thin silicone rubber which is quite elastic or of a material of controlled elasticity, such as the silicone rubber coated mesh fabric shown in U.S. Pat. No. 4,201,202.

The necessary seals between the walls 15 and 16 of the sleeve, and between the various components of the system may be made using a suitable adhesive or by other suitable means.

Once the system 10 is implanted and is in its nonpressurized state, the flexible sleeve 11 permits the penis to assume a substantially normal, flaccid position. However, when the chambers 20 of the sleeve 11 are pressurized the sleeve 11 becomes rigid and the penis assumes an erectile position.

The valve 14, which controls the flow of fluid into and out of the sleeve 11, is preferably a normally closed valve which may be opened either by manually squeezing the valve body or the pressure bulb 12. If desired, the valve 14 can be of the type which is either closed by additional manipulation or which does not completely close but which delays the return of fluid to the reservoir for a suitable period of time. A suitable valve is disclosed in Uson U.S. Pat. No. 4,009,711.

The valve 14 may also be provided with a relief valve feature so that if the pressure in the chambers 20 of the sleeve 11 exceeds a safe level, the valve 14 will automatically open to release the excessive pressure. The relief valve feature also makes it possible to quickly depressurize the sleeve by exerting a strong squeezing force on the penis. A suitable valve with a relief valve feature is shown in Finney U.S. Pat. No. 4,364,379.

In a preferred embodiment of the sleeve of the present invention, the outer wall 16 is of limited distensibility and the chambers 20, even when nonpressurized, are substantially filled with pressurizing fluid. Thus, the amount of fluid needed to completely fill, pressurize and rigidize the chambers 20 is minimized. As a result, the pressure bulb 12 can be relatively small in size, approximately 10 to 15 cc in volume, and thus, can be conveniently implanted in the scrotal sac, if desired, replacing a testicle.

The term "substantially filled" as used herein to describe the fluid content of a chamber means that a chamber contains about 60% to about 95% or more of its capacity of a noncompressible fluid such as water, saline or a free flowing gel. The actual content of fluid can vary; however, the implant when "substantially filled" should be still sufficiently flexible so that the penis can assume a normal flaccid position.

The pressure bulb 12 which is of flexible resilient material can be provided with a small, integral resealable valve (not shown), if desired, so that additional fluid can be added to the closed system with a hypodermic needle after the system has been implanted. A suitable resealable valve is disclosed in Sanders et al. U.S. Pat. No. 3,919,724.

All of the parts and components of the prosthesis are preferably made of or covered with medical grade silicone rubber which is non-reactive, non-toxic and well tolerated by the adjacent organic tissues. Silicone rubber is preferred because it is quite resistant to wear and remains functional for long periods of time. However, other suitable materials, such as an aliphatis polyether polyurethane, possessing desirable properties may also be employed.

Figure 4:
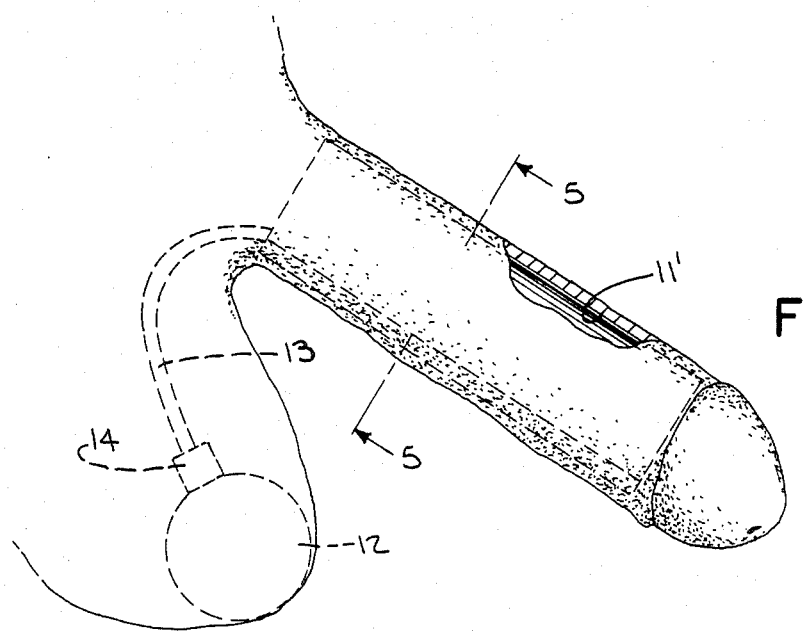
Figure 5:
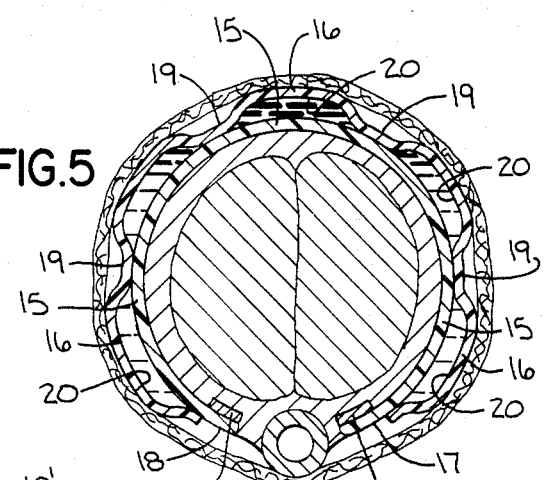
FIG. 5 is a cross sectional view taken along the line 5—5 in FIG. 4.

The surgical procedure for implanting the embodiment of FIG. 1 is quite simple. The penile skin is incised all around, about 0.5 cm. from the coronal groove in circumcised men, and pulled back to the end of the shaft as seen in FIG. 3. The sleeve is positioned around the penile shaft and the edges are then sutured to each other using the nonabsorbable suture strips and sutures. The proximal end of the implant is sutured to the arcuate pubic ligament and its distal end will be inserted between the tip of the corporae and the glans after undermining a clevage between them. The distal end of the implant will then be sutured to the tunica albuginea of the corpus. In this way both ends of the implant will be fixed to both ends of the penis and when inflated it will stretch the penile shaft in all its length. The bulb 12 is inserted easily in the scrotum through a passage dissected between the pulled back skin and the radix penis, to the scrotum. The implanted system is shown in FIGS. 4 and 5.

Figure 6:
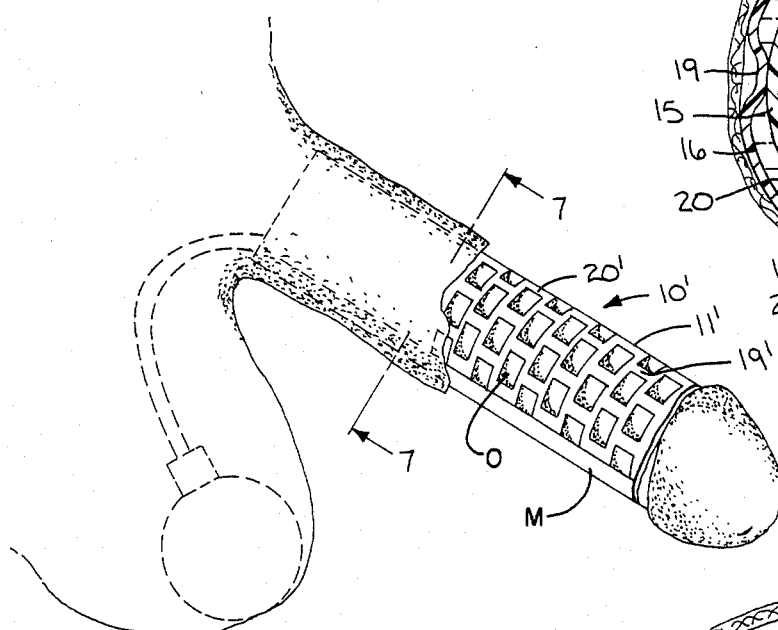
FIG. 6 is a perspective view similar to that of FIG. 1 showing a second embodiment of the system of the present invention.
Figure 7:
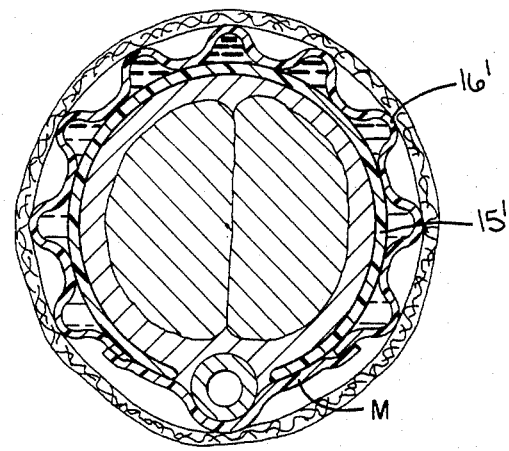
FIG. 7 is a cross sectional view taken along the line 7—7 in FIG. 6.

In FIGS. 6 and 7, a second embodiment of the invention is shown. The system 10' shown therein differs from the embodiment of FIGS. 1 to 5 described in several aspects. Instead of the sleeve 11' having longitudinally divided chambers, it has a single large pressurizable chamber 20' which is formed by sealing together the inner wall 15' and the outer wall 16' to form a mesh-like structure which has openings O which permit the ingrowth of tissue to anchor the implant in place without the need for suturing. The embodiment of FIGS. 6 and 7 also differs from the embodiment of FIGS. 1 and 5 in that the edges 17' and 18' of the sleeve 11' are joined together by a membrane M (seen only in FIG. 7). The membrane M makes the suturing together of the ends of the sleeve 11' unnecessary. The system of FIGS. 6 and 7 is implanted in a manner similar to that previously described.

It will be apparent to those skilled in the art that the penile erectile system of the present invention possesses several unique advantages. One advantage is that the superficial site of the implanted sleeve makes possible the early diagnosis of any leaks or deformities. Another advantage is that the system leaves intact the spongy tissues in the corpora cavornosa of the patient, thus both creating the possibility of using the system as an adjunct in the treatment in psychogenic impotents and making the operation reversible. In such cases, when the patient can achieve a normal erection, the system can be taken out easily without leaving an important scar. Still another advantage of the system is that it may be implanted as an adjunct in elderly men that cannot achieve full erections, as well as in men who have had a total loss of their ability to have an erection for various reasons, including spinal cord injury patients.

It is to be understood that the foregoing description has been for purposes of illustration and that a number of modifications and changes may be made without departing from the spirit and scope of the present invention. For example, the sleeve may be made in other shapes and sizes than those shown and described and other pumps and valves can be used. Therefore, it is to be understood that the invention is not to be limited by any of the specific embodiments described but only by the claims which follow:

We claim:

1. A penile erectile system for treating impotency in man, said system comprising:
    (a) a sleeve of biocompatible material for implanting about a penile shaft beneath the penile skin, between the shaft and the skin, said sleeve having at least one pressurizable chamber;
    (b) pressurizing means for pressurizing said chamber to make it rigid, said means comprising a fluid reservoir for pressurizing fluid and a pump;
    (c) valve means for controlling the flow of fluid between the pressurizing means and the pressurizable chamber; and
    (d) tubing connecting the pressurizing means to the pressurizable chamber.

2. A system of claim 1 in which the pressurizing means is a pressure bulb.

3. A system of claim 1 in which the valve means contains an excess pressure relief feature which causes it to automatically open when the fluid pressure in the chamber exceeds a predetermined safe level.

4. A system of claim 1 in which the sleeve has a plurality of interconnected chambers.

5. A system of claim 1 in which the sleeve is provided with anchoring means for securing it in place about the penile shaft.

6. A system of claim 1 in which said sleeve includes apertures for the ingrowth of tissue to anchor the sleeve in place.

7. A system of claim 1 in which said sleeve is provided with suture tabs for anchoring the sleeve in place.

8. A system of claim 1 in which said chamber of the sleeve has a first relatively inelastic inner wall and a second relatively elastic outer wall.

9. A system of claim 1 in which the sleeve is substantially filled with pressurizing fluid even in its unpressurized state.

10. A system of claim 1 in which the system is a closed system which includes resealable means for introducing or withdrawing pressurizing fluid.

11. A method of surgically treating erectile impotency, without removing spongy tissue in the corpora cavernosa, said method comprising: implanting a sleeve with a pressurizable chamber about the penile shaft of a patient beneath the penile skin, and implanting elsewhere in the patient's body pressurizing means for pressurizing said chamber, a valve for controlling the flow of pressurizing fluid and tubing connecting the pressurizing means to the chamber, said pressurizing means being implanted where it can be readily activated from outside the body to pressurize the chamber and achieve a penile erection.

* * * * *